US00PP19768P3

(12) United States Plant Patent
Laviana

(10) Patent No.: US PP19,768 P3
(45) Date of Patent: Feb. 24, 2009

(54) ***POLEMONIUM* PLANT NAMED 'TOUCH OF CLASS'**

(50) Latin Name: *Polemonium reptans*
Varietal Denomination: Touch of Class

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 0 days.

(21) Appl. No.: 11/900,353

(22) Filed: Sep. 11, 2007

(65) Prior Publication Data

US 2008/0148459 P1 Jun. 19, 2008

Related U.S. Application Data

(60) Provisional application No. 60/857,460, filed on Nov. 7, 2006.

(51) Int. Cl.
*A01H 5/00* (2006.01)

(52) U.S. Cl. ..... Plt./470

(58) Field of Classification Search ..... Plt./470
See application file for complete search history.

*Primary Examiner*—Annette H Para
*Assistant Examiner*—June Hwu
(74) *Attorney, Agent, or Firm*—Penny J. Aguirre

(57) ABSTRACT

A new cultivar of *Polemonium* plant, 'Touch of Class', characterized by its mound of white and green variegated leaves and its abundance of light violet flowers emerging in late spring to early summer.

2 Drawing Sheets

Botanical classification: *Polemonium reptans.*
Variety denomination: 'Touch of Class'.

BACKGROUND OF THE INVENTION

The present invention relates to a new and distinct cultivar of *Polemonium* plant, botanically known as *Polemonium reptans* 'Touch of Class' and will be referred to hereinafter by its cultivar name, 'Touch of Class'. The new cultivar of *Polemonium* is a hardy herbaceous perennial grown for landscape use.

'Touch of Class' was discovered in April of 2005 as a naturally occurring branch mutation of *Polemonium reptans* 'Stairway to Heaven' (U.S. Plant Pat. No. 15,187) in a container in his nursery in Kensington, Conn.

Asexual reproduction of the new cultivar was first accomplished by in vitro propagation in June of 2005 in Kensington, Conn. Propagation by division and tissue culture has determined the characteristics to be stable and reproduced true to type in successive generations.

SUMMARY OF THE INVENTION

The following traits have been repeatedly observed and are determined to be the characteristics of the new cultivar. These attributes in combination distinguish 'Touch of Class' as a unique cultivar of *Polemonium.*

1. 'Touch of Class' exhibits foliage that is variegated with green and white. Leaves with green centers and white margins are typical while some leaves are pure white or with a small patch of green. An intermediate grey green color is occasionally present
2. 'Touch of Class' exhibits an abundance of light violet colored flowers from late April to early June in Connecticut.

In comparison to the parent plant, 'Stairway to Heaven', 'Touch of Class' is similar in plant habit and in having similar variegated foliage, however 'Touch of Class' exhibits a greater number of flowers, blooms longer and the leaf variegation of 'Touch of Class' is white and green whereas the variegation of 'Stairway to Heaven' is green, white and yellow. The species, *Polemonium reptans,* has foliage that is non-variegated. There are other known *Polemonium* cultivars with variegated foliage, however they are cultivars of *Polemonium caeruleum,* a taller species with a more upright plant habit.

BRIEF DESCRIPTION OF THE DRAWINGS

The accompanying colored photographs illustrate the overall appearance and distinct characteristics of the new *Polemonium.* The photograph in FIG. 1 was taken of two year-old plants as grown outdoors in one gallon containers Kensington, Conn. The photograph in FIG. 2 shows a close up of the foliage on six month-old plants that were greenhouse grown in Kensington, Conn. from plugs derived from tissue culture. The colors in the photograph are as close as possible with the photographic and printing technology utilized. The color values cited in the detailed botanical description accurately describe the colors of the new *Polemonium.*

DETAILED BOTANICAL DESCRIPTION

Figure 1:
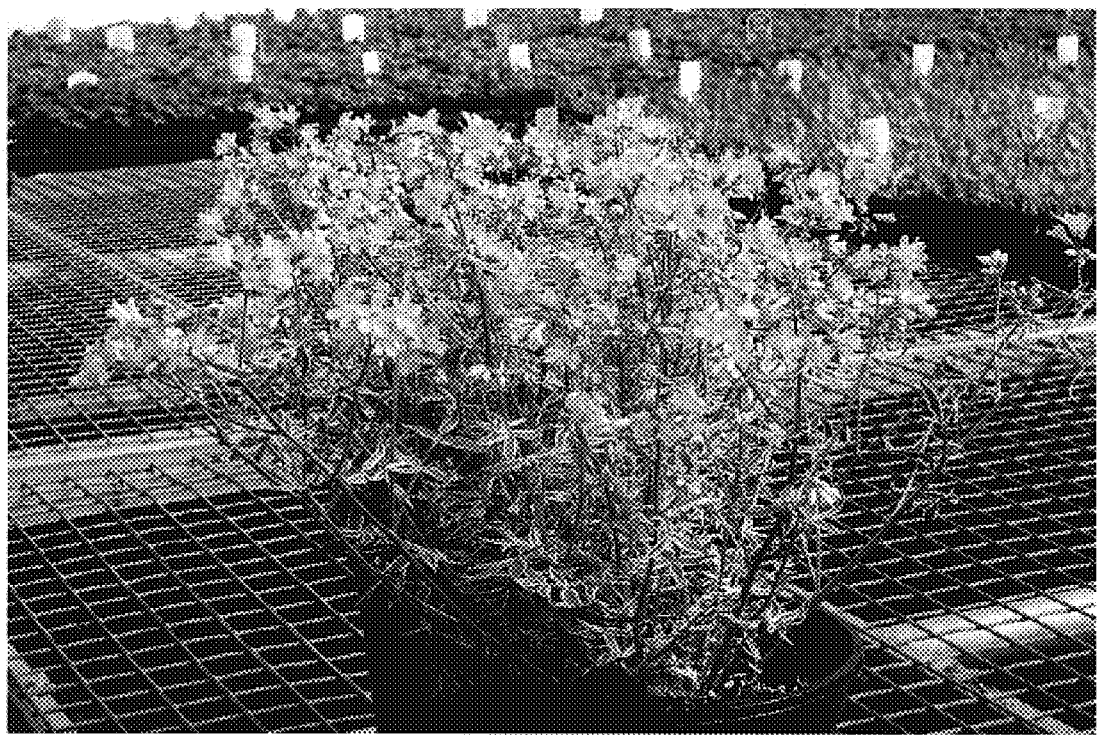
Figure 2:
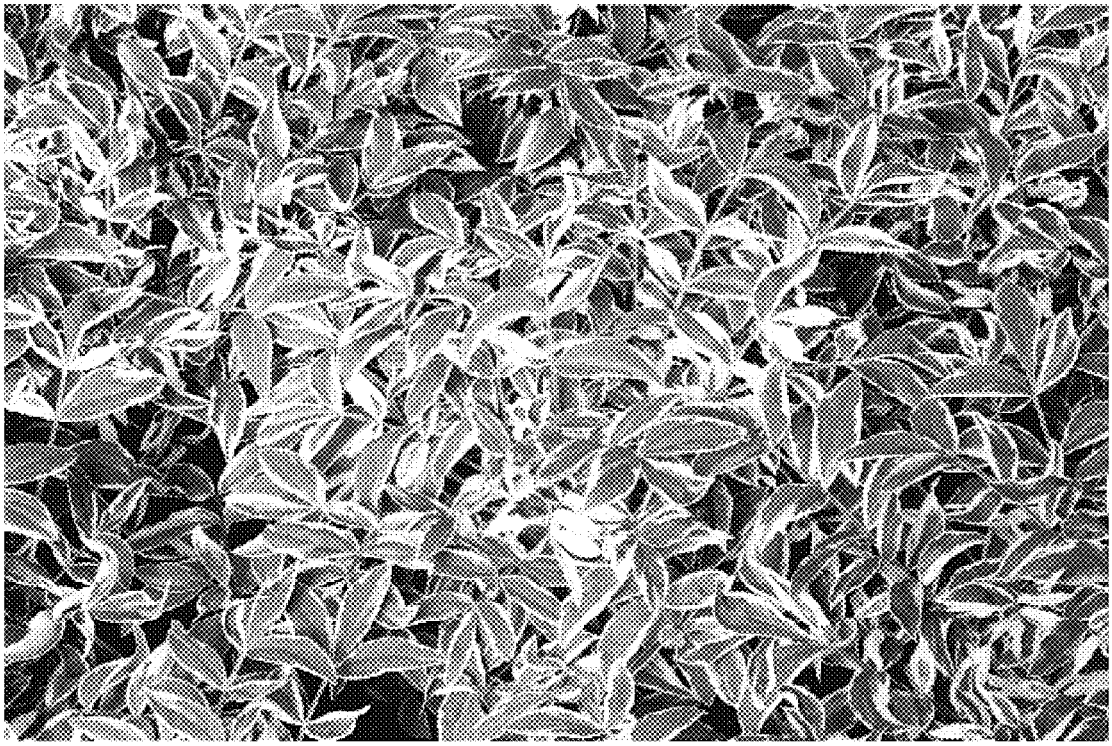

The following is a detailed description of two year old plants of the new cultivar as grown outdoors in for Kensington, Conn. The phenotype of the new cultivar may vary with variations in environmental, climatic, and cultural conditions, as it has not been tested under all possible environmental conditions. The color determination is in accordance with the 2001 RHS Colour Chart of the Royal Horticultural Society, London, England, except where general color terms of ordinary dictionary significance are used.

Botanical classification: 'Touch of Class' is a cultivar of *Polemonium reptans.*

Parentage: Naturally occurring branch mutation of *Polemonium reptans* 'Stairway to Heaven'.

General description:

*Blooming period.*—About 4 weeks between late April to early June in Kensington, Conn.

*Plant habit.*—Herbaceous perennial, mounded, flowering stems emerging from basal leaves.

*Height and spread.*—Matures to 30 to 40 cm in height and 35 to 45 cm in width.

*Hardiness.*—U.S.D.A. Zones 3 to 9.

*Culture.*—Performs best in soils with adequate moisture and fertility in partial shade; new foliage is continuously produced until frost.

*Diseases and pests.*—No susceptibility or resistance to diseases or pests has been observed.

*Root description.*—Fleshy to fibrous emerging from rhizomes.

*Propagation.*—Rhizome division and tissue culture.

*Growth rate.*—Vigorous and reliable perennial.

Foliage description:

*Leaf division.*—Compound, odd-pinnate.

*Leaf arrangement.*—Basal and opposite to slightly opposite on cauline leaves.

*Leaf shape.*—Oblanceolate in outline (both basal and cauline leaves).

*Leaf size.*—Basal leaves range from 15 to 25 cm in length and 5 to 10 cm in width and cauline leaves are an average of 7 in length and 2.5 cm in width.

*Leaflet number.*—Average of 12 per basal leaves and 5 on cauline leaves.

*Leaflet base.*—Cuneate.

*Leaflet apex.*—Cuspidate.

*Leaflet margin.*—Entire.

*Leaflet venation.*—Tri-nerved, matched leaflet color.

*Leaflet surface.*—Glabrous on upper surface and glabrous to pubescent on lower surface.

*Leaflet internode length.*—Average of 1.6 cm.

*Leaflet variegation pattern.*—Typically green centers with a white margin with margin ranging from 1 to 4 mm, on mature leaves an intermediate area is blended into the margin and center with an irregular pattern, less frequently (especially on lower leaves) the leaves are all white or with a narrow center spot of green.

*Leaflet color.*—Newly formed and mature basal foliage upper surface; 137B with margin and all white leaves 155B and intermediate areas 138B, newly formed and mature basal foliage lower surface; 138B with margin and all white leaves 155B, newly formed and mature cauline foliage upper surface; 137B with margin and all white leaves 155B and intermediate areas 138B, newly formed and mature cauline foliage lower surface; 138B with margin and all white leaves 155B.

*Leaflet size.*—Basal leaves; up to 5.5 cm in length and 2.2 cm in width, cauline leaves; up to 2.5 cm in length and 1.5 cm in width.

*Rachis.*—Up to 21 cm in length including petiole with an average width of 2 mm, upper surface is concave, texture is glabrous, 144A in color.

*Petiole.*—Average of 8 cm in length and 3 mm in length, 144A in color.

*Foliage fragrance.*—None.

Flower description:

*Inflorescence type.*—Corymbs of 4 to 7 bell-shaped flowers with an average of 3 corymbs per stem.

*Lastingness of inflorescence.*—About 4 weeks from first opening bloom to fading of last opening bloom, individual blooms last about one week.

*Flower shape.*—Bell-shaped.

*Flower number.*—Average of 20 per flowering stem.

*Flower fragrance.*—None detected.

*Flower buds.*—Conical in shape, about 6 mm in length and 3 mm in diameter, color N155B with shading of 76A (esp. near apex) and stripes of 138B.

*Flower size.*—About 1.2 cm in length and about 1.5 cm in diameter.

*Peduncles.*—1 to 2.5 cm in length and about 0.7 mm in width, 138B in color, glabrous surface.

*Petioles.*—Up to 7 mm in length and about 0.5 mm in width, 138A in color, surface texture is glabrous and slightly shiny.

*Calyx.*—Campanulate, comprised of 5 partially fused sepals, about 9 mm in length and 4 mm in width, persistent.

*Sepals.*—5, 9 mm in length and 2 mm in width, 155A in color with stripes of 138B, glabrous surface, base fused on lower half, attenuate apex, entire margin.

*Corolla form.*—Rotate.

*Petals.*—Oblanceolate in shape, margin entire and slightly dentate near apex, rounded apex, truncate base, color 91B to 91D becoming lighter and translucent near base, glabrous surface.

Reproductive organs:

*Gynoecium.*—1 Pistil, style is about 1 cm in length, 0.3 mm in width and 155C in color, stigma is tri-fid with arms reflexed and 155C in color, ovary is superior, compound, globose in shape, 138C in color.

*Androecium.*—5 stamens, filament is 155C in color, 8 mm in length, 0.3 mm in width, base is adnate to petals, anthers are 1 mm in length and width, attachment is basifixed, translucent and 145C in color, pollen not visible.

*Fruit.*—Fruit and seed production was not observed under the conditions tested.

I claim:

1. A new and distinct variety of *Polemonium* plant designated 'Touch of Class' as described and illustrated herein.

* * * * *